United States Patent [19]

Ogata et al.

[11] Patent Number: 4,851,572
[45] Date of Patent: Jul. 25, 1989

[54] γ-L-GLUTAMYL-4-NITROANILIDE DERIVATIVES AND PROCESS FOR DETERMINING γ-GTP ACTIVITY USING THE SAME

[75] Inventors: Hiroshi Ogata, Tokyo; Hiroyoshi Nawa, Fujimi; Kuniaki Tokuda; Masami Ishihara, both of Kawagoe, all of Japan

[73] Assignee: Wako Pure Chemical Industries, Ltd., Osaka, Japan

[21] Appl. No.: 214,343

[22] Filed: Jul. 1, 1988

[30] Foreign Application Priority Data

Jul. 3, 1987 [JP] Japan ................. 62-166642

[51] Int. Cl.$^4$ ........................... C07C 103/50
[52] U.S. Cl. ........................... 562/437; 435/4; 435/16
[58] Field of Search ............... 562/437; 435/4, 16

[56] References Cited

U.S. PATENT DOCUMENTS

| | | | |
|---|---|---|---|
| 3,979,447 | 11/1973 | Bernt et al. | 260/518 |
| 3,986,931 | 8/1975 | Bernt et al. | 195/103 |
| 4,049,702 | 7/1975 | Bernt et al. | 260/501 |
| 4,675,290 | 6/1987 | Matsumoto et al. | 435/16 |

FOREIGN PATENT DOCUMENTS 2259512 6/1974 Fed. Rep. of Germany .
2823342 12/1978 Fed. Rep. of Germany .

OTHER PUBLICATIONS

Chemical Abstracts, vol. 104, No. 9, Mar. 3, 1986, Columbus, Ohio USA, Yamasato Fujio et al. "Measurement of Gama-Glutamyl Transpeptidase Activity", p. 329, column 2, abstract-No. 64 809u, & Jpn. Kokai Tokyo Koho JP 60-160 896 [85-160 896].

Primary Examiner—James H. Reamer
Attorney, Agent, or Firm—Armstrong, Nikaido, Marmelstein, Kubovcik & Murray

[57] ABSTRACT

A γ-L-glutamyl-4-nitroanilide derivative of the formula:

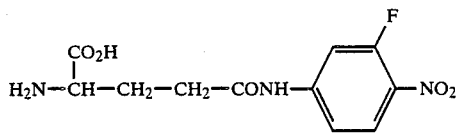

wherein R is a lower hydroxyalkyl group, is suitable as a substrate for determining γ-GTP activity.

5 Claims, 2 Drawing Sheets

γ-L-GLUTAMYL-4-NITROANILIDE DERIVATIVES AND PROCESS FOR DETERMINING γ-GTP ACTIVITY USING THE SAME

BACKGROUND OF THE INVENTION

This invention relates to a novel γ-L-glutamyl-4-nitroanilide derivative which is useful as a substrate for determining γ-glutamyl transpeptidase (hereinafter abbreviated as γ-GTP) activity, and a process for determining γ-GTP activity using the same.

γ-GTP is a membrane-bound enzyme which has activity to hydrolyze γ-glutamylpeptide to transfer the γ-glutamyl group to other peptides or amino acids.

Determination of γ-GTP activity is widely utilized, for example, for diagnosis of liver and file duct diseases and screening of alcoholism. Recently, a γ-GTP isozyme which appears specifically in serum of a hepatoma patient has been found, and the relationship between γ-GTP in urine and pathosis has been reported. Thus, the diagnostic significance of determination of γ-GTP activity is noted again.

As a process for determining γ-GTP activity, various processes have so far been proposed and made practicable, and a rate assay method using γ-L-glutamyl-p-nitroanilide as a substrate is the most usual and is now often employed.

However, γ-L-glutamyl-p-nitroanilide as a substrate is disadvantageous in that it is slightly soluble in a suitable pH range for determining γ-GTP activity and is unstable in such a suitable pH range for dissolution.

On the other hand, as water-soluble substrates free from these disadvantages, there are γ-L-glutamyl-3-carboxy-4-nitroanilide, γ-L-glutamyl-3-sulfo-4-nitroanilide, etc. (the specifications of U.S. Pat. Nos. 3, 979,447, 3,986,931 and 4,049,702). These water-soluble substrates are much superior to γ-glutamyl-p-nitroanilide in both solubility and stability after dissolution, but they are not always sufficient in stability after dissolution. Thus, their improvement has been desired.

In determination of γ-GTP activity in human serum, serum containing a known concentration of γ-GTP (control serum) is often used as a standard or a maker for quality control. As the γ-GTP added to such control serum, those derived from bovine kidney and porline kidney are mainly used. There is a high possibility of the presence of serum hepatitis virus in human serum having a high γ-GTP activity, and so purification of γ-GTP from the human serum is difficult from a hygienic viewpoint. A human tissue containing a large amount of γ-GTP is not easily available. For these reasons, γ-GTPs derived from bovine kidney and procine kidney are used in place of human serum γ-GTP. However, such water-soluble substrates as described above have a more strongly polar group (a water-soluble group) than does γ-L-glutamyl-p-nitroanilide. Therefore, they tend to vary in reactivity as substrates, depending on the electrically charged state of γ-GTP particularly in the vicinity of the active site, and they vary considerably in reactivity with γ-GTP as substrates, depending on the source of γ-GTP such as human liver, bovine kidney, porcine kidney, etc. That is to say, when the activity value (international unit (IU)/l) of γ-GTP in a sample prepared by dissolving γ-GTP derived from each of the above-mentioned various sources in a predetermined concentration (M) is measured by use of the abovementioned water-soluble substrate, the difference among the activity values thus measured is considerably large. Therefore, in the case of determining γ-GTP in human serum by use of a control serum containing γ-GTP derived from bovine kidney and/or porcine kidney as a standard or a maker for quality control, employment of the above-mentioned water-soluble substrate has been disadvantageous in that the control serum should be controlled more strictly, as compared with a conventional determination method using γ-L-glutamyl-p-nitroanilide as a substrate.

SUMMARY OF THE INVENTION

This invention has been made in consideration of such conditions and is intended to provide a novel substrate for determining γ-GTP activity which is soluble in water, is excellent in stability after dissolution, and has a small difference in reactivity with γ-GTPs derived from various sources; and a process for determining γ-GTP activity using said substrate.

This invention provides a γ-L-glutamyl-4-nitroanilide derivative represented by the general formula:

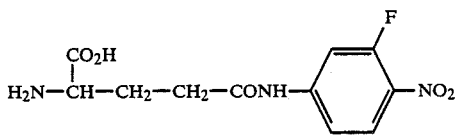

wherein R is a lower hydroxyalkyl group, and a process for determining γ-GTP activity using said derivative as a substrate.

DESCRIPTION OF THE PREFERRED EMBODIMENTS

Figure 1:
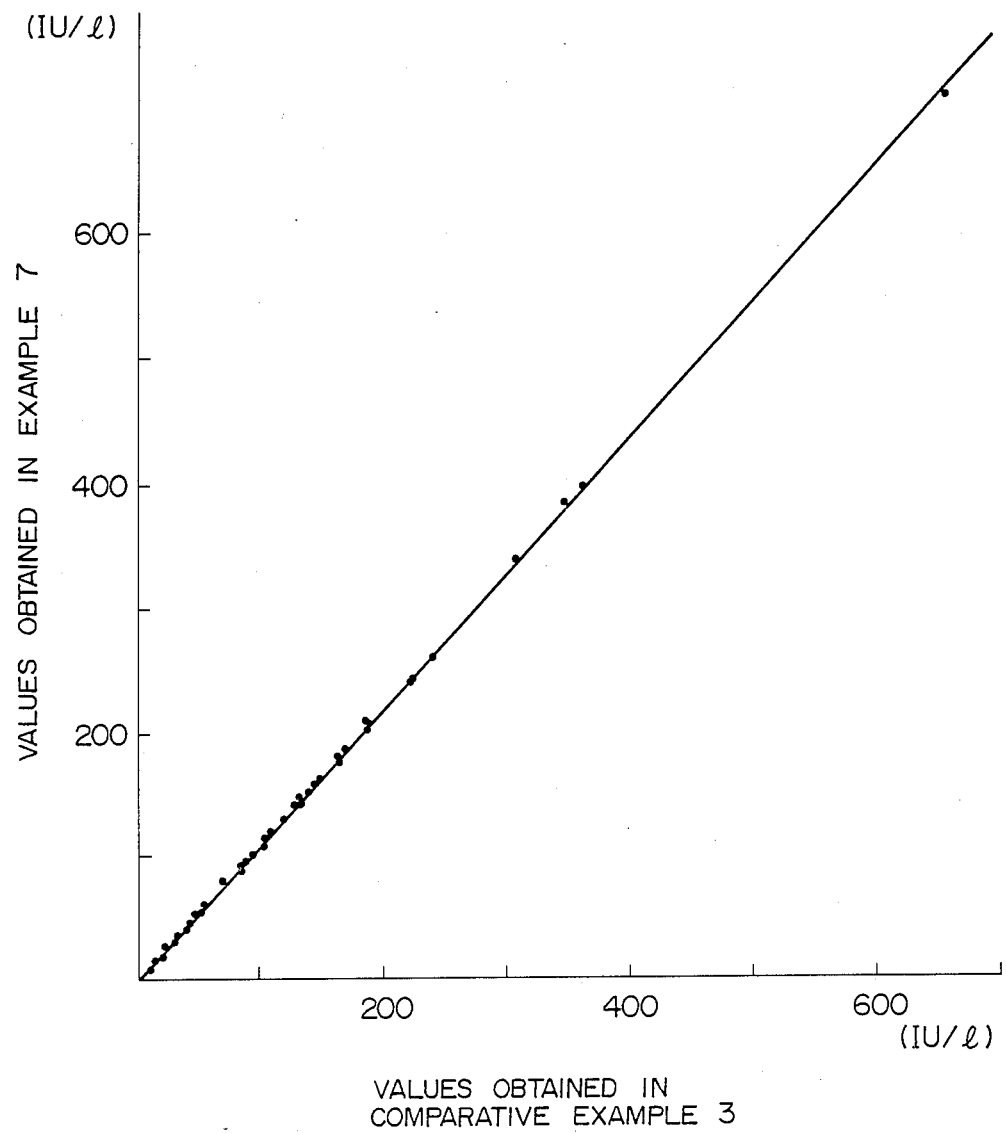
FIG. 1 shows the correlation between the values measured for individual human sera in Example 7 and those in Comparative Example 3: the axis of abscissa refers to the values obtained in Comparative Example 3 and the axis of ordinate to the values obtained in Example 7.

The γ-L-glutamyl-4-nitroanilide derivative of the formula:

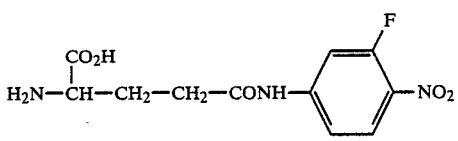

wherein R is a loswer hydroxyalkyl group which may have two or more hydroxyl groups and have preferably 1 to 4 carbon atoms, is a novel compound which has not been known in any literature.

The novel compound of this invention is characterized in that the water-soluble group attached at the ortho position in relation to the nitro group is a hydroxyalkyl group which has a very low polarity, unlike carboxyl group and sulfonic acid group.

In the compound of this invention of the above general formula, the lower hydroxyalkyl group represented by R includes, for example, lower hydroxyalkyl groups having 1 to 4 carbon atoms such as hydroxymethyl, 1-hydroxyethyl, 2-hydroxyethyl, 1-hydroxypropyl, 2-hydroxypropyl, 3-hydroxypropyl, 1,2-dihydroxypropyl, 1,3-dihydroxypropyl, 2,3-dihydroxypropyl, 1,4-dihydroxybutyl, 2,3-dihydroxybutyl, 3,4-dihydroxybutyl, and the like.

The compound of this invention can easily be synthesized by reacting a corresponding 4-nitroaniline derivative with a N-protected L-glutamic acid derivative whose carboxyl group has been activated, such as N-phthaloyl-L-glutamic anhydride, in an organic solvent such as dioxane or dimethyl sulfoxide, and then removing the amino-protecting group by use of hydrazine or the like.

The 4-nitroanilide derivative as intermediate material can easily be synthesized by acylating a corresponding aniline derivative, thereafter nitrating the same, isolating the N-acylated derivative which has been nitrated at a desired position, and then hydrolyzing this derivative to remove the acyl group.

The γ-L-glutamyl-4-nitroanilide derivative of this invention is excellent in water solubility and stability after dissolution because it has a hydroxyl group through a lower hydrocarbon group at the ortho position in relation to the nitro group. Moreover, it is highly reactive with γ-GTP and has a small difference in reactivities with γ-GTPs derived from various sources because the hydroxyalkyl group is a very weakly polar group unlike carboxyl group and sulfonic acid group. It has such excellent characteristics as a substrate and is an excellent substrate for determining γ-GTP activity.

In the process for determining γ-GTP activity of this invention, it is sufficient that γ-GTP activity is measured according to a conventional process for determining γ-GTP using γ-glutamyl-p-nitroanilide as a substrate, except for using the γ-L-glutamyl-4-nitroanilide derivative of this invention as a substrate. In detail, it is sufficient that γ-GTP activity is measured, for example, by using the γ-L-glutamyl-4-nitroanilide derivative of this invention as a substrate, carrying out a reaction between the substrate and a sample such as human serum, human urine, etc. in a suitable buffer solution in the presence of a glutamic acid acceptor such as glycylglycine, and measuring γ-GTP activity, for example, by an initial rate measuring method (rate assay, etc.). The rate assay can be carried out, for example, by directly measuring an absorbance of a 4-nitroaniline derivative generated by the action of γ-GTP, or measuring an absorbance of a dye which is produced by coupling the 4-nitroaniline derivative with a p-dialkylaminobenzaldehyde, a p-dialkylaminocinnamaldehyde, or the like.

Amino acids such as glutamic acid and the like may optionally be added to reagents previously in order to reduce an influence of inhibition caused by amino acids in serum as a sample. The determination conditions such as buffer solution, the pH of reaction solution, the amounts of substrate and acceptor, measuring temperature, measuring wavelength, and the like may be in accordance with a conventional method.

The substrate of this invention has various characteristics which conventional standard substrates for determining γ-GTP activity, such as γ-L-glutamyl-p-nitroanilide and γ-L-glutamyl-3-carboxy-4-nitroanilide cannot have at the same time, and it is excellent in all of water solubility, stability after dissolution and reactivity with γ-GTP. Therefore, it has quite satisfactory effects as a very excellent substrate for determining γ-GTP activity, compared with a conventional standard substrate.

Examples are described below but are not by way of limitation but by way of illustration.

EXAMPLE 1

Synthesis of γ-L-glutamyl-3-hydroxymethyl-4-nitroanilide

In 81.6 g of acetic anhydride was dissolved 24.6 g of 3-aminobenzyl alcohol, and the reaction was carried out with refluxing for 3 hours. After completion of the reaction, after-treatment was conducted by a conventional method to obtain 34.6 g of crystals of 3-acetoxymethylacetanilide.

M.p. 81°–83° C.

To 300 ml of acetic anhydride was added 56 g of concentrated nitric acid (α=1.42), and 32.0 g of the 3-acetoxymethylacetanilide obtained in the above was dissolved in them, after which the resulting solution was subjected to reaction at 14° to 16° C. for 2 hours. After completion of the reaction, the reaction product was extracted therefrom by a conventional method and 37.9 g of the extracted oily substance was purified by a column chromatography and then crystallized to obtain 9.7 g of crystals of 3-acetoxymethyl-4-nitroacetanilide.

M.p. 110° C.

In 100 ml of 2N hydrochloric acid was dissolved 9.7 g of the thus obtained 3-acetoxymethyl-4-nitroacetanilide with heating, and the reaction was carried out with refluxing for 0.5 hour, after which after-treatment was conducted by a conventional method to obtain 5.4 g of crystals of 3-hydroxymethyl-4-nitroaniline.

M.p. 143°~145° C.

UV λmax: 382 nm, ε=1.28×10$^4$ (H$_2$O).

IR νcm$^{-1}$ (KBr): 3460, 3360 (NH$_2$), 3250 (OH), 1340 (NO$_2$).

NMR δppm (Acetone-d$_6$): 2.95 (2H, s, —CH$_2$OH), 4.50 (1H, d, —CH$_2$OH̲), 6.00 (2H, br., —NH̲$_2$), 6.50~6.90

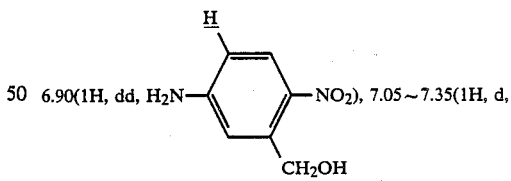

6.90(1H, dd,

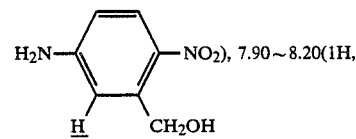

7.05~7.35(1H, d, 7.90~8.20(1H,

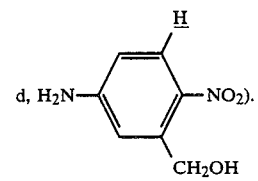

d,

To the whole 3-hydroxymethyl-4-nitroaniline obtained were added 11.8 g of N-phthaloyl-L-glutamic anhydride and 30 ml of dioxane, and they were heated to prepare a solution, after which the reaction was carried out with refluxing for 7 hours. After completion of the reaction, after-treatment was conducted by a conventional method to obtain 11.8 g of crystals of N-phthaloyl-γ-L-glutamyl-3-hydroxymethyl-4-nitroanilide.

M.p. 211°–213° C.

The whole N-phthaloyl-γ-L-glutamyl-3-hydroxymethyl-4-nitroanilide obtained was dissolved in 140 ml of methanol, followed by adding thereto 4.6 g of 80% hydrazine hydrate, and after stirring at 17° to 20° C. for 5 hours, the resulting solution was allowed to stand overnight. After completion of the reaction, after-treatment was conducted by a conventional method to obtain 5.7 g of crystals of γ-L-glutamyl-3-hydroxymethyl-4-nitroanilide.

M.p. 156° C. (dec).

UV λmax: 317 nm, ε=1.01×10⁴ (H₂O).

IR νcm⁻¹ (KBr): 3400 (NH, NH₂), 3230 (OH), 1680 (CO), 1620 (COOH), 1320, 1500 (NO₂).

NMR δppm (DMSO-d₆): 1.7~2.3 (2H, br., —CHCH₂CH₂—), 2.3~3.0 (2H, br., —CHCH₂CH₂—), 3.1~3.7 (1H, br., —CHCH₂CH₂—), 4.8 (2H, s, —CH₂OH), 5.5~8.0 (4H, br., NH₂, CONH, OH), 7.5~8.2 (3H, m, phenyl), 10.5~11.5 (1H, br., —COOH).

EXAMPLE 2

Synthesis of γ-L-glutamyl-3-(α-hydroxyethyl)-4-nitroanilide

In 35 ml of acetic anhydride was dissolved 12.3 g of 3-(α-hydroxyethyl)aniline, and the reaction was carried out at 105° to 110° C. for 1.5 hours. After completion of the reaction, the reaction product was extracted from the reaction solution by a conventional method to obtain 20 g of an oily substance containing 3-(α-acetoxyethyl)acetanilide.

To 19 g of the oily substance obtained was added 100 ml of acetic anhydride, followed by adding thereto 21 ml of concentrated nitric acid (α=1.42) at 0° to 10° C., and the reaction carried out at the same temperature for 4 hours. After completion of the reaction, the reaction product was extracted from the reaction solution by a conventional method, and from 19 g of the extracted oily substance, 1.8 g of an oily substance of 3-(α-acetoxyethyl)-4-nitroacetanilide was obtained by a column chromatography.

The whole 3-(α-acetoxyethyl)-4-nitroacetanilide obtained was dissolved in 10 ml of 2N hydrochloric acid with heating, and the resulting solution was subjected to reaction at 99° to 101° C. for 1 hour. After completion of the reaction, the reaction product was extracted therefrom by a conventional method to obtain 1.1 g of an oily substance of 3-(α-hydroxyethyl)-4-nitroaniline.

UV λmax: 380 mn, ε=0.96×10⁴ (H₂O).

NMR δppm (DMSO-d₆): 1.55 (3, d, —CH₃), 5.0(1H, m, —OH), 5.3~5.7(1H, m, —CHCH₃), 5.8~6.3

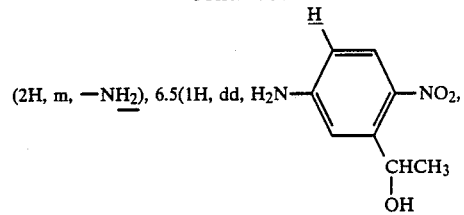

(2H, m, —NH₂), 6.5(1H, dd, H₂N—⌬—NO₂, CHCH₃, OH

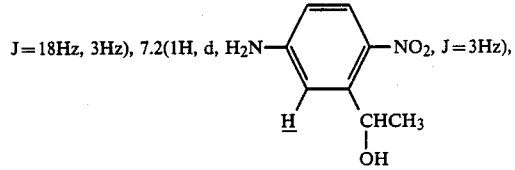

J=18Hz, 3Hz), 7.2(1H, d, H₂N—⌬—NO₂, J=3Hz),

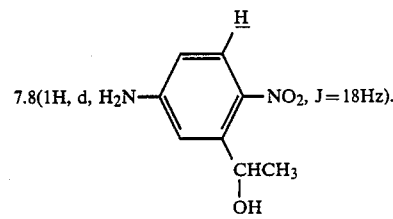

7.8(1H, d, H₂N—⌬—NO₂, J=18Hz).

To 1.1 g of the 3-(α-hydroxyethyl)-4-nitroaniline were added 1.9 g of N-phthaloyl-L-glutamic anhydride and 20 ml of dioxane, and they were heated to prepare a solution, which was then subjected to reaction at 90° to 95° C. for 3.5 hours. After completion of the reaction, after-treatment was conducted by a conventional method to obtain 2.7 g of a viscous, oily substance of N-phthaloyl-γ-L-glutamyl-3-(α-hydroxyethyl)-4-nitroanilide.

The whole N-phthaloyl-γ-L-glutamyl-3-(α-hydroxyethyl)-4-nitroanilide obtained was dissolved in 30 ml of methanol, followed by adding thereto 0.5 ml of 80% hydrazine hydrate, and after stirring at 18° to 20° C. for 4 hours, the resulting solution was allowed to stand overnight. After completion of the reaction, after-treatment was conducted by a conventional method to obtain 0.5 g of crystals of γ-L-glutamyl-3-(α-hydroxyethyl)-4-nitroanilide.

M.p. 160° C. (dec)

UV λmax: 306 nm, ε=0.52×10⁴ (H₂O).

NMR δppm (DMSO-d₆): 1.35 (3H, d, —CH₃),

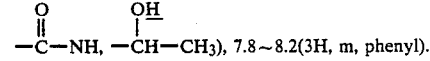

1.5~3.0(4H, m, —CHCH₂CH₂C—), 3.0~3.5(1H, m,

—CHCH₂CH₂C—), 4.5~6.2(6H, br., —COOH, —NH₂,

—C(=O)—NH, —CH(OH)—CH₃), 7.8~8.2(3H, m, phenyl).

EXAMPLE 3

Synthesis of γ-L-glutamyl-3-(β-hydroxyethyl)-4-nitroanilide

In 30 ml of acetic anhydride was dissolved 10.3 g of 3-(β-hydroxyethyl)aniline, and the reaction was carried out at 109° to 112° C. for 0.5 hour. After completion of the reaction, the reaction product was extracted from the reaction solution by a conventional method to obtain 17.2 g of an oily substance containing 3-(β-acetoxyethyl)acetanilide.

To 140 ml of acetic anhydride was added 27 g of concentrated nitric acid (d=1.42), followed by adding thereto a solution prepared by dissolving 17.0 g of the 3-(β-acetoxyethyl)acetanilide obtained in the above in 15 ml of acetic anhydride, and the reaction was carried out at 14° to 16° C. for 2 hours. After completion of the reaction, the reaction product was extracted from the reaction solution by a conventional method, and 18 g of the extracted oily substance was purified by a column chromatography and crystallized to obtain 1.7 g of crystals of 3-(β-acetoxyethyl)-4-nitroacetanilide.

M.p. 137°–139° C.

In 16 ml of 2N hydrochloric acid was dissolved 1.6 g of the thus obtained 3-(β-acetoxyethyl)-4-nitroacetanilide with heating, and the resulting solution was subjected to reaction at 99° to 101° C. for 0.5 hour. After completion of the reaction, the reaction product was extracted therefrom and then purified by a conventional method to obtain 0.88 g of crystals of 3-(β-hydroxyethyl)-4-nitroaniline.

M.p. 95°–86° C.

UV $\lambda$max: 381 nm, $\epsilon=1.09\times10^4$ (H$_2$O).

IR $\nu$cm$^{-1}$ (KBr): 3460 (OH), 3230, 3350 (NH$_2$), 1305 (NO$_2$).

NMR $\delta$ppm (CDCl$_3$+DMSO-d$_6$): 3.2 (2H, t, —C$\underline{H}_2$CH$_2$OH), 3.8 (1H, br., —O$\underline{H}$), 3.9 (2H, t, —CH$_2$C$\underline{H}_2$OH), 5.3 (2H, br., —N$\underline{H}_2$), 6.4–8.1 (3H, m, phenyl).

To 0.80 g of the 3-(β-hydroxyethyl)-4-nitroaniline obtained were added 1.59 g of N-phthaloyl-L-glutamic anhydride and 15 ml of dioxane, and they were heated to prepare a solution, which was then subjected to reaction at 95° C. for 4 hours. After completion of the reaction, purification by a column chromatography was conducted, followed by crystallization, whereby 1.4 g of crystals of N-phthaloyl-γ-L-glutamyl-3-(β-hydroxyethyl)-4-nitroanilide was obtained.

M.p. 70°–95° C.

In 15 ml of methanol was dissolved 1.3 g of the N-phthaloyl-γ-L-glutamyl-3-(β-hydroxyethyl)-4-nitroanilide obtained, followed by adding thereto 0.5 g of 80% hydrazine hydrate, and after stirring at 24° to 26° C. for 5 hours, the resulting solution was allowed to stand overnight. After completion of the reaction, after-treatment was conducted by a conventional method to obtain 0.52 g of crystals of γ-L-glutamyl-3-(β-hydroxyethyl)-4-nitroanilide.

M.p. 164°–167° C.

UV $\lambda$max: 309 nm, $\epsilon=0.816\times10^4$ (H$_2$O).

IR $\nu$cm$^{-1}$ (KBr): 3450 (OH), 2320, 3250 (NH$_2$), 1680 (CONH), 1620 (COOH), 1345, 1505 (NO$_2$).

NMR $\delta$ppm (DMSO-d$_6$): 1.8–2.4 (2H, br., —CHC$\underline{H}_2$CH$_2$O), 2.4–2.9 (2H, br., —CHCH$_2$C$\underline{H}_2$—), 2.9–3.3 (2H, t, —C$\underline{H}_2$CH$_2$OH), 3.3–3.9 (3$\underline{H}$, m, —CH$_2$C$\underline{H}_2$OH, —CH$\underline{CH}_2$CH$_2$—), 5.5–8.0 (5H, br., —N$\underline{H}_2$C$\underline{H}_2$, —COO$\underline{H}$, —CON$\underline{H}$—, —CH$_2$CH$_2$O$\underline{H}$), 7.5–8.1 (3H, m, phenyl).

EXAMPLE 4

Synthesis of γ-L-glutamyl-3-hydroxymethyl-4-nitroanilide

In 81.6 g of acetic anhydride was dissolved 24.6 g of 3-aminobenzyl alcohol, and the reaction was carried out with refluxing for 3 hours. After completion of the reaction, after-treatment was conducted by a conventional method to obtain 34.6 g of crystals of 3-acetoxymethylacetanilide.

To a mixed solution of 150 ml of glacial acetic acid and 150 ml of concentrated sulfuric acid was added 56 g of concentrated nitric acid (d=1.42), and 32.0 g of the 3-acetoxymethylacetanilide obtained in the above was dissolved therein, after which the resulting solution was subjected to reaction at 5° to 10° C. for 2 hours. After completion of the reaction, the reaction product was extracted therefrom by a conventional method, and 57.5 g of the extracted oily substance was recrystallized from 700 ml of toluene to obtain 17.5 g of crystals of 3-acetoxymethyl-4-nitroacetanilide.

In 180 ml of 2N hydrochloric acid was dissolved 17.5 g of the thus obtained 3-acetoxymethyl-4-nitroacetanilide with heating, and the reaction was carried out with refluxing for 0.5 hour, after which after-treatment by a conventional method to obtain 9.7 g of crystals of 3-hydroxymethyl-4-nitroaniline.

To the whole 3-hydroxymethyl-4-nitroaniline obtained were added 21.3 g of N-phthaloyl-L-glutamic anhydride and 55 ml of dioxane, and they were heated to prepare a solution, which was then subjected to reaction with refluxing for 7 hours. After completion of the reaction, after-treatment was conducted by a conventional method to obtain 21.3 g of crystals of N-phthaloyl-γ-L-glutamyl-3-hydroxymethyl-4-nitroanilide.

The whole N-phthaloyl-γ-L-glutamyl-3-hydroxymethyl-4-nitroanilide obtained was dissolved in 250 ml of methanol, followed by adding thereto 8.3 g of 80% hydrazine hydrate, and after stirring at 17° to 20° C. for 5 hours, the resulting solution was allowed to stand overnight. After completion of the reaction, after-treatment was conducted to obtain 10.3 g of crystals of γ-L-glutamyl-3-hydroxymethyl-4-nitroanilide.

Physical properties of the individual compounds obtained were the same as those of the compounds obtained in Example 1.

EXAMPLE 5

Measurement of γ-GTP activity

[Preparation of reagent solutions]

① Buffer solution

100 Millimols of tris(hydroxymethyl)aminomethane and 60 mmols of glycylglycine were added in 800 ml of deionized water, and pH of its solution was adjusted to 8.2 (at 25° C.) with hydrochloric acid, after which the resulting solution was made up to 1 liter with deionized water.

② Substrate solution

In deionized water was dissolved 15 mmols of the γ-L-glutamyl-3-hydroxymethyl-4-nitroanilide obtained in Example 1 to make a total volume of 1 liter.

[Samples]

As samples, there were used human serum and 7% aqueous bovine albumin solutions containing γ-GTP derived from porcine kidney or bovine kidney (hereinafter abbreviated as parcine sample and bovine sample, respectively).

[Measuring method]

To 50 μl of each sample was added 2.0 ml of the buffer solution ①, followed by preincubation at 37° C. for 3 minutes, and 0.5 ml of the substrate solution ② was added. After sufficient mixing, the resulting mixture was allowed to stand for 1 minute, after which the increase rate of absorbance at 410 nm was measured, and the γ-GTP activity value (IU/l) in the sample was calculated from the molecular absorption coefficient ($7.6 \times 10^6$ cm²/mol) of 3-hydroxymethyl-4-nitroaniline generated.

EXAMPLE 6

Measurement of γ-GTP activity
[Preparation of reagent solutions]
① Buffer solution
100 mmols of tris(hydroxymethyl)aminomethane and 60 mmols of glycylglycine were added in 800 ml of deionized water, and pH of its solution was adjusted to 8.2 (at 25° C.) with hydrochloric acid, after which the resulting solution was made up to 1 liter with deionized water.
② Substrate solution
In deionized water was dissolved 15 mmols of the γ-L-glutamyl-3-(β-hydroxyethyl)-4-nitroanilide obtained in Example 3 to make a total volume of 1 liter.
[Samples]
The same samples as in Example 5 were used.
[Measuring method]
To 50 μl of each sample was added 2.0 ml of the buffer solution ①, followed by preincubation at 37° C. for 3 minutes, and 0.5 ml of the substrate solution ② was added. After sufficient mixing, the resulting mixture was allowed to stand for 1 minute, after which the increase rate of absorbance at 410 nm was measured, and the γ-GTP activity value (IU/l) in the sample was calculated from the molecular absorption coefficient ($7.3 \times 10^6$ cm²/mol) of 3-(β-hydroxyethyl)-4-nitroaniline generated.

COMPARATIVE EXAMPLE 1

Measurement of γ-GTP activity
[Preparation of reagent solutions]
① Buffer solution
100 mmols of tris(hydroxymethyl)aminomethane and 60 mmols of glycylglycine were added in 800 ml of deionized water, and pH of its solution was adjusted to 8.4 (at 25° C.) with hydrochloric acid, after which the resulting solution was made up to 1 liter with deionized water.
② Substrate solution
In 100 ml of 1N sulfuric acid solution was dissolved 20 mmols of γ-L-glutamyl-p-nitroanilide, and the resulting solution was made up to 1 liter with deionized water.

The compositions of the above-mentioned reagent solutions were in accordance with those of the respective reagent solution for γ-GTP B-AR II (a trade name, Wako Pure Chemical Industries, Ltd.).
[Samples]
The same samples as in Example 5 were used. [Measuring method]
To 50 μl of each sample was added 2.0 ml of the buffer solution ①, followed by preincubation at 37° C. for 3 minutes, and 0.5 ml of the substrate solution ② was added. After sufficient mixing, the resulting mixture was allowed to stand for 1 minute, after which the increase rate of absorbance at 410 nm was measured, and the γ-GTP activity value (IU/l) in the sample was calculated from the molecular absorption coefficient ($8.8 \times 10^6$ cm²/mol) of p-nitroaniline generated.

COMPARATIVE EXAMPLE 2

Measurement of γ-GTP activity
[Preparation of reagent solutions]
① Buffer solution
100 mmols of tris(hydroxymethyl)aminomethane and 100 mmols of glycylglycine were added in 800 ml of deionized water, and pH of its solution was adjusted to 8.2 (at 25° C.) with hydrochloric acid, after which the resulting solution was made up to 1 liter with deionized water.
② Substrate solution
In 100 mM glycylglycine buffer (pH 8.2) was dissolved 14.5 mmols of γ-L-glutamyl-3-carboxy-4-nitroanilide ammonium salt to make a total volume of 1 liter.

The compositions of the above-mentioned reagent solutions were in accordance with those of γ-GT Reagents 1 and 2 (trade names, Boehringer Mannheim Yamanouchi Co., Ltd.).
[Samples]
The same samples as in Example 5 were used.
[Measuring method]
To 50 μl of each sample was added 2.0 ml of the buffer solution ①, followed by preincubation at 37° C. for 3 minutes, and 0.5 ml of the subdrate solution ② was added. After sufficient mixing, the resulting mixture was allowed to stand for 1 minute, after which the increase rate of absorbance at 410 nm was measured, and the γ-GTP activity value (IU/l) in the sample was calculated from the molecular absorption coefficient ($7.9 \times 10^6$/mol) of 3-carboxy-4-nitroaniline generated.

The results obtained in Examples 5 and 6 and Comparative Examples 1 and 2 are shown in Table 1.

TABLE 1

| | Sample | | | Difference between max. and min. activity values. |
|---|---|---|---|---|
| | Human serum | Porcine sample | Bovine sample | |
| Comparative Example 1 | 100 (Standard) | 100 (Standard) | 100 (Standard) | — |
| Comparative Example 2 | 103 | 127 | 94 | 33 |
| Example 5 | 148 | 139 | 151 | 12 |
| Example 6 | 95 | 87 | 85 | 10 |

In Table 1, the values of Comparative Example 2 and Examples 5 and 6 are relative γ-GTP activity values taking those of Comparative Example 1 as 100. The γ-GTP activity values (IU/l) were calculated from an absorbance change (ΔE/5 min) at 410 nm for 5 minutes after initiation of the reaction.

In Table 2 are shown the solubility of the substrates for measuring γ-GTP activity used in Examples 5 and 6 and Comparative Examples 1 and 2 in reagent solutions (reagent solutions being obtained by mixing each buffer solution and each substrate solution in the ratio of 4:1), and the results of stability test on the substrate solutions in the individual cases.

TABLE 2

| | | Stability | |
|---|---|---|---|
| Substrate | Solubility | 5° C. | Room temp. |
| γ-L-glutamyl-p-nitroanilide (Comparative Example 1) | 37° C., pH 8.2 5 mM | Crystals were precipitated | Crystals were precipitated |
| γ-L-glutamyl-3-carboxy-4-nitroanilide (Comparative Example 2) | 5° C., pH 8.2 100 mM ↑ | 0053 | 0166 |
| γ-L-glutamyl- | | | |

TABLE 2-continued

| Substrate | Solubility | Stability 5° C. | Room temp. |
|---|---|---|---|
| 3-hydroxymethyl-4-nitroanilide (Example 5) | 5° C., pH 8.2 100 mM ↑ | 0003 | 0074 |
| γ-L-glutamyl-3-(β-hydroxyethyl)-4-nitroanilide (Example 6) | 5° C., pH 8.2 10 mM | 0001 | 0049 |

Note:
Each figure in the "stability" column indicates an increase of absorbance at 410 nm per mmol of each substrate after 2 weeks from the preparation of the substrate solution.

In Table 3 are shown the results of measuring, by a conventional method, Km values of γ-L-glutamyl-3-hydroxymethyl-4-nitroanilide, which is a compound of this invention, for each of γ-GTPs derived from human serum, porcine kidney and bovine kidney.

In Table 3 are also shown, for reference, Km values of γ-L-glutamyl-3-carboxy-4-nitroanilide and γ-L-glutamyl-p-nitroanilide reported by Leslie M. Shaw (Clinical Chemistry, 23, 79 (1977)).

TABLE 3

| | Km value (mM) Source of γ-GTP | | |
|---|---|---|---|
| Substrate | Human serum | Porcine kidney | Bovine kidney |
| γ-L-glutamyl-3-hydroxymethyl-4-nitroanilide | 0.94 | 0.67 | 0.67 |
| γ-L-glutamyl-p-nitroanilide (comparison) | 1.33 | 1.87 | — |
| γ-L-glutamyl-3-carboxy-4-nitroanilide (comparison) | 1.19 | 1.63 | — |

It can be seen that as is clear from Tables 1, 2 and 3, the compound of this invention is sufficiently reactive with γ-GTP as a substrate and has a small difference in reactivity with γ-GTPs derived from various sources.

Further, the results shown in Table 3 indicate that substrates having a relatively strongly polar, water-soluble group, such as γ-L-glutamyl-3-carboxy-4-nitroanilide vary more widely in reactivity with γ-GTPs derived from various sources than substrates having no water-soluble group, such as γ-L-glutamyl-p-nitroanilide, or substrates having a weakly polar, water-soluble group (a hydroxyalkyl group), such as the compound of this invention. It is estimated that this is because when a substrate and the enzyme react with each other, they are mutually seriously affected each other by their electrically charged states. That is to say, it seems probable that since the electrically charged state of the enzyme particularly in the vicinity of the active site varies depending on the source of the enzyme, the substrates having a strongly polar, water-soluble group are seriously affected in reactivity with the enzyme derived from each source.

The substrate of this invention has a water-solubility sufficiently larger than that required for practical purpose, i.e., 5 mmols. A solution of this substrate is far more stable than solutions of conventional substrates both when stored at room temperature (20° to 25° C.) and when kept in cold storage (5° C.). When kept in cold storage, the solution of this substrate can be used for at least three months without any trouble in practice.

EXAMPLE 7

[Preparation of reagent solutions]
① Buffer solution (R1)
The buffer solution prepared in Example 5 was used.
② Substrate solution (R2)
In deionized water was dissolved 10 mmols of the γ-L-glutamyl-3-hydroxymethyl-4-nitroanilide obtained in Example 4 to make a total volume of 1 liter.

[Samples]
Fifty human sera were used as samples.

[Measuring method]
Measurement was carried out by using a Hitachi automatic analyzer Model 7150 under the conditions shown in Table 4.

TABLE 4

| CHEMISTRY PARAMETERS | |
|---|---|
| ASSAY CODE | [RATE-A]:[30]–[50] |
| SAMPLE VOLUME | [6] |
| R1 VOLUME | [320] [100] [NO] |
| R2 VOLUME | [80] [20] [NO] |
| WAVE LENGTH | [505] [405] |
| CALIB. METHOD | [K FACTOR*] [0] [0] |
| STD. (1) CONC.-POS. | [0]–[1] |
| STD. (2-6) CONC.-POS | [0]—[0] |
| SD LIMIT | [↓] |
| DUPLICATE LIMIT | [10000] |
| SENSITIVITY LIMIT | [0] |
| ABS. LIMIT (INC/DEC) | [15000] [INCREASE] |
| PROZONE LIMIT | [↓][↓] |
| EXPECTED VALUE | [ ][ ] |
| PANIC VALUE | [ ][ ] |
| INSTRUMENT FACTOR | [1.00] |

*K FACTOR = 7725 ($\epsilon$ = 8.76)

[Measurement results]
The results of within-run precision by use of two kinds of samples are shown in Table 5.

TABLE 5

| | Sample | |
|---|---|---|
| | 1 | 2 |
| Number of repetitions (n) | 40 | 40 |
| Maximum (IU/l) | 68 | 139 |
| Minimum (IU/l) | 66 | 134 |
| Average (IU/l) | 66.4 | 137.0 |
| Standard deviation (S.D.) | 0.63 | 1.13 |
| Coefficient of variation (C.V.) | 0.95 | 0.83 |

As is clear from the results shown in Table 5, good precision was shown.

When a calibration curve was prepared by use of a 7% aqueous bovine albumin solution containing γ-GTP derived from porcine kidney, it was found that good linearity could be attained up to about 6400 IU/l.

Comparative Example 3

[Preparation of reagent solutions]
① Buffer solution (R1)
The buffer solution prepared in Comparative Example 2 was used.
② Substrate solution (R2)
The substrate solution prepared in Comparative Example 2 was used.

[Samples]
The same samples as in Example 7 were used.

[Measuring method]

Measurement was carried out under the same conditions as in Example 7, except that among CHEMISTRY PARAMETERS in Table 4, R1 VOLUME was changed to [320][100][NO], R1 VOLUME to [80][20][NO], and K FACTOR to 7123 (ε=9.5).

COMPARATIVE EXAMPLE 4

[Reagent solutions]

The following reagent solutions were prepared according to Recommended method of S.S.C.C.

① Buffer solution (R1)

0.125M Tris-HCL buffer (pH 7.8, at 37° C., containing 96 mM glycylglycine and 13 mM magnesium chloride).

② Substrate solution (R2)

A 0.1N hydrochloric acid solution containing 20 mM of γ-L-glutamyl-4-nitroanilide.

[Samples]

The same samples as in Example 7 were used.

[Measuring method]

Measurement was carried out under the same conditions as in Example 7, except that among CHEMISTRY PARAMETERS in Table 4, K FACTOR was changed to 6835 (ε=9.90).

In FIG. 1 is shown the correlation of the values measured for the individual human sera in Example 7 with those in Comparative Example 3. The coefficient of correlation, the regression equation, and the like, obtained by statistical processing, etc. are shown below.

Number of samples n=50

Coefficient of Correlation γ=0.9998

Regression equation (X: Comparative Example 3, Y: Example 7), Y=1.087X−0.038.

Average values: Comparative Example 3=106.72, Example 7=115.94

Figure 2:
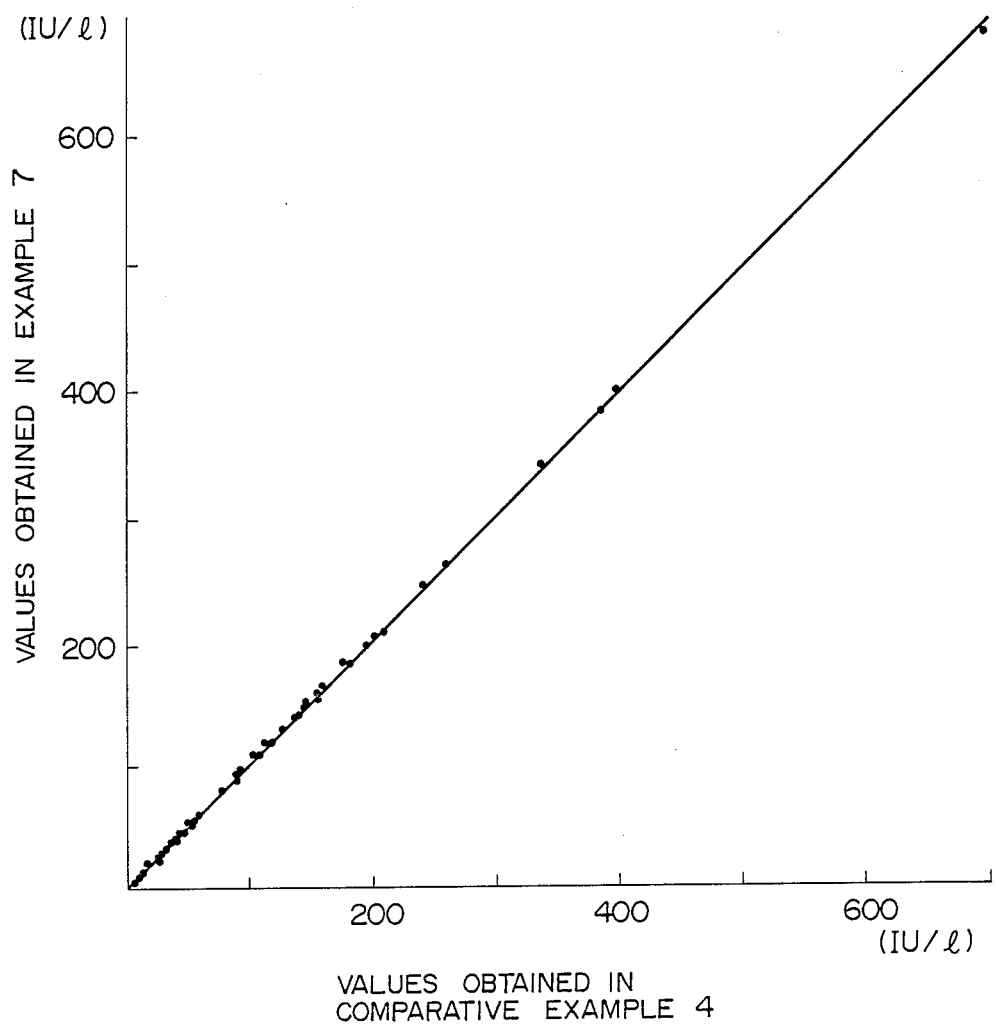
FIG. 2 shows the correlation between the values measured for individual human sera in Example 7 and those in Comparative Example 4: the axis of abscissa refers to the values obtained in Comparative Example 4 and the axis of ordinate to the values obtained in Example 7.

In FIG. 2 is shown the correlation of the values measured for the individual human sera in Example 7 with those in Comparative Example 4. The coefficient of correlation, the regression equation, and the like, obtained by statistical processing, etc. are shown below.

Number of samples n=50

Coefficient of correlation γ=0.9998

Regression equation (X: Comparative Example 4, Y: Example 7), Y=0.985X+2.603

Average values: Comparative Example 4=115.02, Example 7=115.94

It can be seen that as is clear from FIG. 1 and FIG. 2, the values measured by use of the γ-GTP measuring reagent solution using the compound of this invention as a substrate correlates sufficiently with the values measured by the SSCC method using γ-L-glutamyl-p-nitroanilide as a substrate and the values measured by a conventional method using γ-L-glutamyl-3-carboxy-4-nitroanilide as a substrate.

This invention provides a novel γ-L-glutamyl-4-nitroanilide derivative which is useful as a substrate for determining γ-GTP activity, and a process for determining γ-GTP activity using said derivative. A substrate for determining γ-GTP activity compound of the compound of this invention is markedly effective in that it has, for example, the following excellent characteristics as substrate. It is soluble in water, has a high stability after dissolution, is highly reactive with γ-GTP as substrate, and has a small difference in reactivity with γ-GTPs derived from various sources.

What is claimed is:

1. A γ-L-glutamyl-4-nitroanilide derivative represented by the formula:

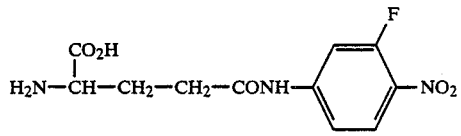

wherein R is a lower hydroxyalkyl group.

2. In a process for determining γ-glutamyl transpeptidase activity in a sample, the improvement which comprises using as a substrate for γ-glutamyl transpeptidase a γ-L-glutamyl-4-nitroanilide derivative represented by the formula:

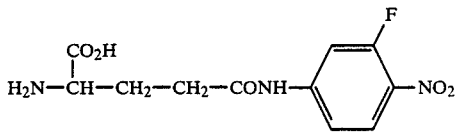

wherein R is a lower hydroxyalkyl group.

3. A γ-L-glutamyl-4-nitroanilide derivative according to claim 1, which is γ-L-glutamyl-3-hydroxymethyl-4-nitroanilide.

4. A γ-L-glutamyl-4-nitroanilide derivative according to claim 1, which is γ-L-glutamyl-3-(α-hydroxyethyl)-4-nitroanilide.

5. A γ-L-glutamyl-4-nitroanilide derivative according to claim 1, which is γ-L-glutamyl-3-(β-hydroxyethyl)-4-nitroanilide.

* * * * *

UNITED STATES PATENT AND TRADEMARK OFFICE
CERTIFICATE OF CORRECTION

PATENT NO. : 4,851,572
DATED : July 25, 1989
INVENTOR(S) : OGATA et al

It is certified that error appears in the above-identified patent and that said Letters Patent is hereby corrected as shown below:

On the cover page, Item [57], "F" attached to the benzene ring, should read --R--.

Column 2, lines 25 to 30, "F" attached to the benzene ring, should read --R--;

lines 55 to 60, "F" attached to the benzene ring, should read --R--.

Column 14, lines 20 to 25, "F" attached to the benzene ring, should read --R--;

lines 34 to 39, "F" attached to the benzene ring, should read --R--.

Signed and Sealed this

Twenty-third Day of July, 1991

Attest:

HARRY F. MANBECK, JR.

*Attesting Officer*  *Commissioner of Patents and Trademarks*